United States Patent [19]
Olsson et al.

[11] Patent Number: 5,273,031
[45] Date of Patent: Dec. 28, 1993

[54] VENTILATOR

[75] Inventors: Sven-Gunnar Olsson, Arloev; Bo Dahlstreom, Vaellingby; Sture Eriksson, Vallentuna; Georgios Psaros, Tullinge, all of Sweden

[73] Assignee: Siemens Aktiengesellschaft, Munich, Fed. Rep. of Germany

[21] Appl. No.: 775,476

[22] Filed: Oct. 15, 1991

[30] Foreign Application Priority Data

Oct. 31, 1990 [SE] Sweden .................................. 9003465

[51] Int. Cl.⁵ ............................................. A61M 16/00
[52] U.S. Cl. ........................... 128/204.18; 128/204.21; 128/205.24
[58] Field of Search ...................... 128/204.18, 204.21, 128/204.23, 205.24

[56] References Cited

U.S. PATENT DOCUMENTS 4,688,565 8/1987 Kobayashi ....................... 128/204.19

FOREIGN PATENT DOCUMENTS 3244574 3/1984 Fed. Rep. of Germany.
225182 2/1969 Sweden.

OTHER PUBLICATIONS

"7200 Series Microprocessor Ventilator" by Puritan-Bennett, Aug. 1988.

Primary Examiner—Edgar S. Burr
Assistant Examiner—Aaron J. Lewis
Attorney, Agent, or Firm—Hill, Steadman & Simpson

[57] ABSTRACT

A ventilator for supplying and emitting respiratory gas to and from the airways of a human or an animal patient has a multiple-function safety valve located between a 10 control valve and the airways. The safety valve is biased in its closing direction by two springs, which apply force that corresponds to a predetermined overpressure, and is biased in its opening direction by a spring loaded piston, which applies force that exceeds the force of the springs. When electrical power is supplied to the ventilator, an electromagnet is energized. The electromagnet pulls the piston against the force of its spring load, and the safety valve closes. By means of a control device, the pressure in an inspiration section of the ventilator can be monitored and the electromagnet is disconnected at a programmed overpressure. In the event of a power failure, the safety valve will open and air can pass through the open safety valve to the airways.

10 Claims, 2 Drawing Sheets

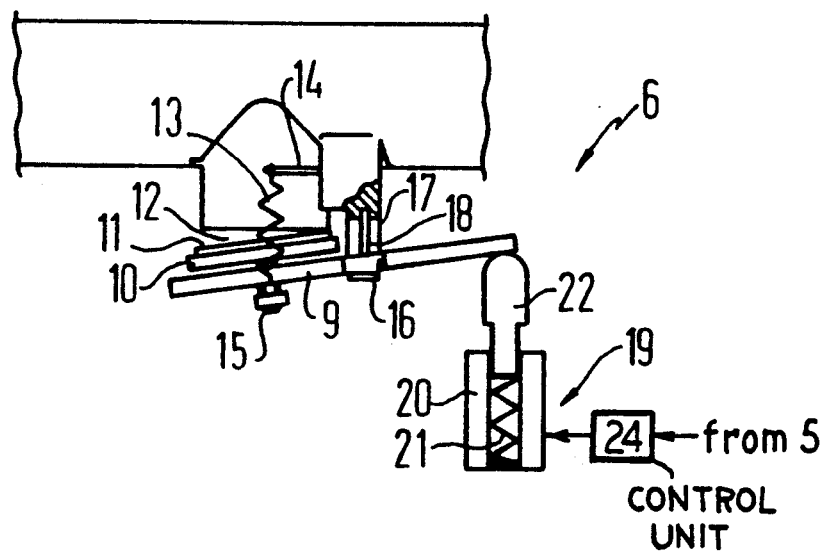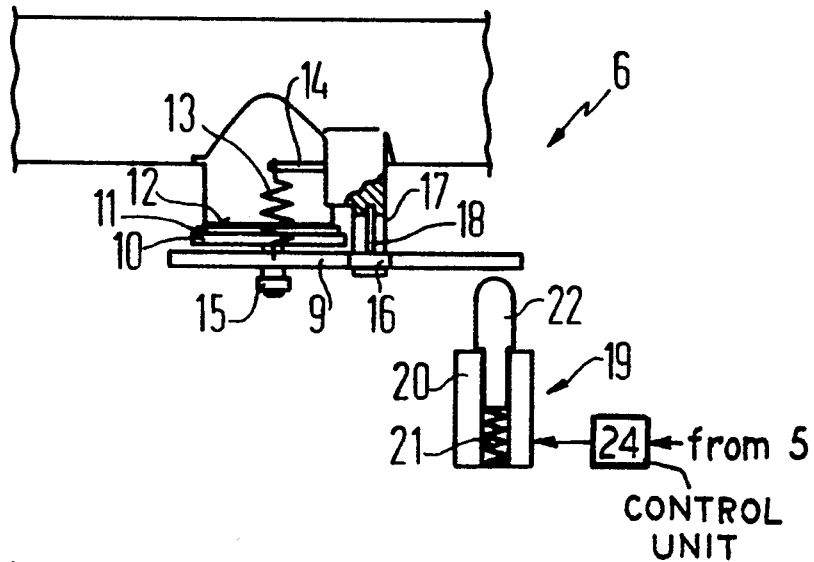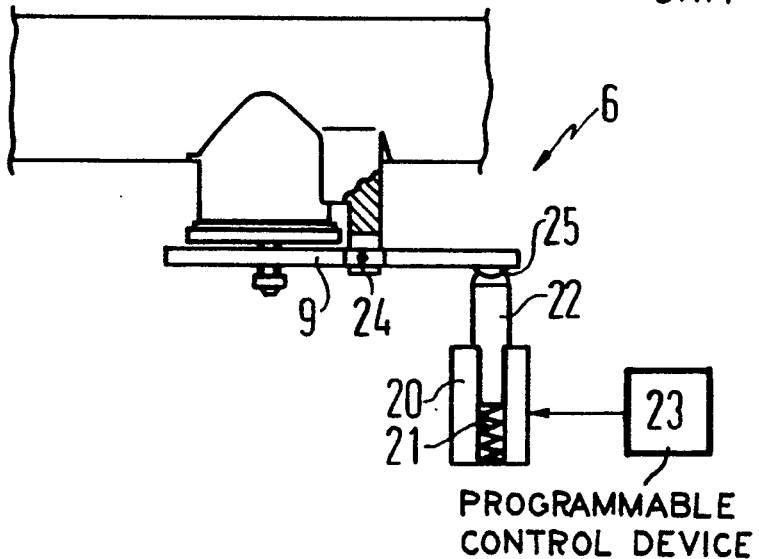

VENTILATOR

BACKGROUND OF THE INVENTION

1. Field of the Invention

The invention relates to a ventilator to be connected to the airways of a human or an animal patient for supplying and emitting respiratory gas to and from the airways, of the type having an inspiration section through which the respiratory gas is supplied to the airways, the inspiration section having at least one control valve for the gas flow and a safety valve, which is biased by a force load in the closing direction and a spring device in the opening direction, the safety valve being located between the control valve and the airways.

2. Description of the Prior Art

A known ventilator (7200 Microprocessor Ventilator, Puritan Bennett Corp., USA) is provided with an inspiration section, which is supplied with air and any additional gas from a compressed-air system. The respiratory gas passes through a system of control valves in order to obtain a desired pressure. To prevent an undesirable high pressure in the lungs of a patient, the inspiration section is provided with a safety valve between the control valves and the patient. The safety valve is described in the ventilator service manual, pages 80-82 and accompanying drawing and includes a valve that is biased in the opening direction by a spring and in the closing direction by an overpressure caused by air from the compressed-air system, adjusted to a pressure corresponding to the pressure of the spring plus the maximum allowed pressure for the patient. The amount of closing pressure is dependent on the pressure of the compressed-air system, because the valve that admits the pressure to the safety valve only has two fixed positions: open and closed. The safety valve thus opens at an overpressure that exceeds the maximum allowed pressure for the patient. Furthermore, the safety valve automatically opens in the event of a power failure and upon a shortage of pressure from the compressed-air system, which makes it possible for the patient to get air through the open safety valve.

As the closing force of the safety valve is dependent on a valve, there are risks for operational disturbances, should this valve become inoperative. The closing pressure could, for example, disappear if the valve ceases to function, and the safety valve would then open completely in spite of a correct respiratory gas pressure with respect to the patient.

SUMMARY OF THE INVENTION

An object of the present invention is to provide a ventilator such that known safety functions are retained, but are improved upon and such that the disadvantages are overcome and the construction is simplified and made safer.

This object is achieved in accordance with the principles of the present invention in a ventilator having a safety valve with a valve cover biased in its closing direction by a force load and in its open direction by an electromagnetically operated spring device. The force from the spring device exceeds the force from the force load (or more precisely, the torque experienced by the valve cover as a result of the force from the spring device exceeds the torque experienced by the valve cover as a result of the force load). The force load is produced by at least one spring, whose spring constant is selected such that the force load corresponds to a predetermined overpressure in the inspiration section. An electromagnet removes the bias of the spring device on the safety valve when supplied with current. Thus, the safety valve is closed when the electromagnet is energized and open when the electromagnet is de-energized.

The safety valve will be in an open position until the electromagnet is energized, whereupon the safety valve assumes its position as an overpressure protection. Upon a loss of current as occurs during, for example, a power failure, the safety valve immediately opens because the electromagnet then is de-energized and the patient will get air via the open safety valve. As this system is completely independent of the compressed air supplied, the maximum overpressure allowed is well defined and the safety valve stays closed as long as the pressure of the respiratory gas is below the maximum pressure.

By providing the safety valve with an adjustment device for the force load, for example a tightening screw for the spring, a fine adjustment of the maximum allowed overpressure can be achieved, or alternatively a variation with certain limits.

An alternative solution is obtained in accordance with the invention in that the force load is generated by an electromagnet, whereby the force may be controlled by the current supply to the electromagnet so that it corresponds to the force from the spring device plus a force corresponding to a predetermined overpressure in the inspiration section.

In this embodiment, all the functions and advantages of the first solution are obtained, but with fewer structural parts. With this solution, it is possible to adjust, even more accurately and within wider limits, the defined overpressure at which the safety valve shall open by varying the current to the electromagnet.

It is advantageous to have the ventilator of both embodiments include a device for sensing the pressure in the inspiration section and to have the electromagnet disconnected at an adjustable overpressure, which is lower than the predetermined overpressure. The disconnection of the electromagnet may be achieved by a programmable control device, which disconnects the electromagnet at a programmed overpressure. In order to prevent occasional transitory peaks in the variation of the pressure from unnecessarily opening the safety valve, it is appropriate if the electromagnet is not disconnected until the pressure exceeds the adjustable/programmable overpressure plus a predetermined safety interval.

It is an extra advantage of the ventilator that it can be adapted to each individual patient so that a programmed overpressure replaces the predetermined overpressure. The electromagnet will then be disconnected and the safety valve will open at the programmed overpressure.

DESCRIPTION OF THE DRAWINGS

FIG. 2 shows a safety valve of the pneumatic unit of FIG. 1 in its open position.

FIG. 3 shows the safety valve of FIG. 2 in its closed position.

FIG. 4 shows an alternative embodiment of a safety valve for the pneumatic unit of FIG. 1.

DESCRIPTION OF THE PREFERRED EMBODIMENTS

Figure 1:
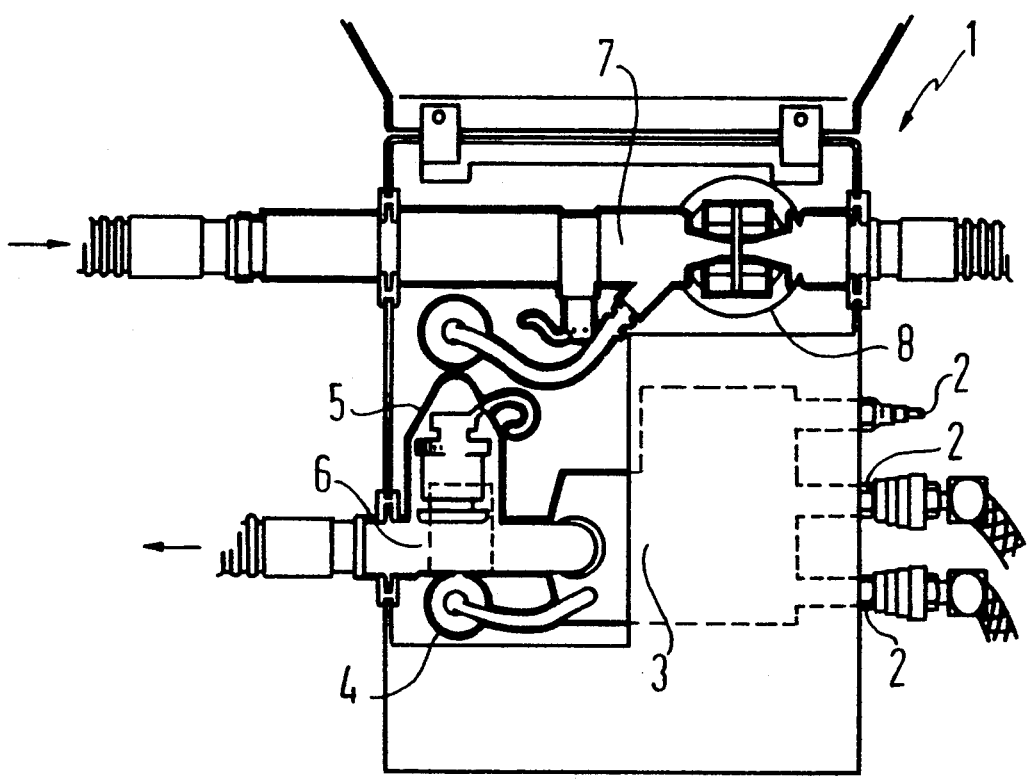
FIG. 1 shows a pneumatic unit of a ventilator, constructed in accordance with the principles of the present invention.

A pneumatic unit 1 of a ventilator as shown in FIG. 1, having several inlets 2 for air and any additional gases, which are supplied under pressure into an inspiration section 3 of the pneumatic unit 1. In the inspiration section 3, the additional gases are mixed with air and supplied to a patient under a controlled pressure and in a measured amount. Upon exciting the pneumatic unit 1, the gas mixture passes through a bacteria filter 4, a pressure transducer 5 and a safety valve 6, which is marked by a broken line and located on the underside of the inspiration section 3.

From the patient, the gas mixture and the expiration gas of the patient are supplied to an expiration section 7 of the pneumatic unit 1. Also in the expiration section 7, the pressure is measured, and an expiration valve 8 regulates the pressure in the expiration section 7 to a desired level. The ventilator also includes a control unit 24 (shown in FIG. 2), by which desired variables and parameters can be set and/or programmed.

The safety valve 6 of the inspiration section 3 has several functions in this construction. It acts as a mechanical overpressure valve, which opens if an undesirably high pressure is accumulated in the inspiration section 3 and thereby prevents the patient from being exposed to gas under pressure which could be injurious. It also acts as a monitoring valve, which opens at a certain programmed overpressure, which is set by a physician, and as an emergency valve, which immediately opens in the event of a power failure, for example, and thereby provides the patient with air via the open valve. To further increase the safety of the patient, the ventilator is constructed such that when the safety valve 6 opens, for any of the mentioned reasons, the expiration valve 8 opens completely and the inspiration section 3 closes.

In order to obtain these functions, the safety valve 6 is of a special construction, which is shown in FIGS. 2 and 3.

A plate 9 is provided at one end with an adjustment plate 10 on which a sealing disk 11 is fastened. The sealing disk 11 fits over the valve opening 12 and is pressed against it by means of two springs 13 (one is concealed by the valve), which are fastened to the plate and to two pins 14 (one is concealed by the valve) located above the valve opening 12.

On the underside of the plate 9, a tightening screw 15 is located, by which the adjustment plate 10 can be moved vertically relative to the plate 9 and thereby enabling the springs 13 to be tightened, by moving of the adjustment plate 10 upwards, or unloaded, by moving the adjustment plate 10 downwards. The overpressure at which the safety valve 6 is to open can thus be varied by varying the tightness (tension) of the springs 13.

To keep the plate 9 in its correct position, two indentations 16 (only one is visible) are cut in the middle of the longitudinal sides of the plate 9, the indentations 16 fitting around two legs 17 (of which one is sectioned to show the construction), which project from the area behind the valve opening 12. Between the two legs 17 are two pins 18 (only one is visible), which form a fulcrum for the plate 9.

At the other end of the plate 9, viewed from the tightening screw 15, an electromagnetic device 19 is located, which includes an electromagnet 20, a spring 2 and a piston 22. The spring 21 presses the piston 22 against the plate 9 when the electromagnet 20 is switched off (de-energized) thereby opening the safety valve 6, as shown in FIG. 2. When the power is switched on, the electromagnet 20 pulls the piston 22 against the spring force of the spring 21 and the safety valve is closed by the spring 13, as shown in FIG. 3.

Thus, the safety valve 6 is normally open, and closes only when the ventilator is in use. Apart from opening when the overpressure is too high, the safety valve 6 also opens in the event of a power failure and enables the patient to breath via the opening 12. By controlling the electromagnetic device 19 by the control unit 24, which receives information about pressure in the inspiration section 3 from the pressure transducer 5, the electromagnet 20 can be switched off at a pressure programmed in the control unit. A physician may hereby adapt the safety level of the pressure for each individual patient.

In FIG. 4, an alternative embodiment of the safety valve 6 is shown. In this embodiment, the piston 22 is mechanically connected 25 to the plate 9, and the plate 9 is rotatably arranged around an axis of rotation (pivot pin) 24. By regulating the current through the electromagnet 20, its pulling force on the piston 22 can be varied to correspond to the predetermined closing pressure of the safety valve, and thus there is no need for the spring 13. The coil current for the electromagnet 20 corresponding to the overpressure at which the safety valve is to open can be selected in a simple manner and at a magnitude selected individually for each patient by means of a programmable control device 23 (which may be an integrated part of the aforementioned control unit 24). To increase the safety of the ventilator in this embodiment, the current through the electromagnet 20 can be limited, so that the closing pressure never exceeds a predetermined maximum overpressure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respiratory ventilator comprising:
   means for supplying and receiving respiratory gas to and from the airways of a patient, including an inspiration section through which said respiratory gas is supplied to said airways;
   at least one control valve in said inspiration section for controlling flow of said respiratory gas; and
   a safety valve disposed between said control valve and said airways for, when open, admitting air to said airways, said safety valve having a valve opening, a valve plate carrying a sealing element, means supporting said valve plate for pivoting between an open position with said sealing element spaced from said valve opening, and a closed position with said sealing element blocking said valve opening, means for applying a force load, corresponding to a predetermined overpressure in said inspiration section, to said plate for generating a first torque urging said plate toward said closed position, said means for applying further including means connected to said plate for adjusting the magnitude of said force load, and electromagnetic means for applying, when de-energized, a force to said plate for generating a second torque urging said plate toward said open position, said second torque exceeding said first torque so that said safety valve is closed when said electromagnetic means is energized and is open when electromagnetic means is de-energized.

2. A respiratory ventilator as claimed in claim 1 wherein said means for applying a force load is at least one spring having one end connected to said valve plate and a fixed opposite end and having a spring constant selected so that said force load corresponds to said predetermined overpressure in said inspiration section.

3. A respiratory ventilator as claimed in claim 2 further comprising:
   means for adjusting the tension of said at least one spring for adjusting the magnitude of said force load.

4. A respiratory ventilator as claimed in claim 1 further comprising:
   means for sensing pressure in said inspiration section; and
   means for de-energizing said electromagnetic means when a selected overpressure in said inspiration section, sensed by said means for sensing, is lower than said predetermined overpressure.

5. A respiratory ventilator as claimed in claim 4 further comprising:
   programmable control means for de-energizing said electromagnetic means at a programmed overpressure which is less than said predetermined overpressure.

6. A respiratory ventilator as claimed in claim 1 further comprising:
   means for sensing pressure in said inspiration section; and
   means for de-energizing said electromagnetic means when an overpressure in said inspiration section, sensed by said means for sensing, exceeds a selected overpressure by a predetermined safety interval and is below said predetermined overpressure.

7. A respiratory ventilator comprising:
   means for supplying and receiving respiratory gas to and from the airways of a patient, including an inspiration section through which said respiratory gas is supplied to said airways;
   at least one control valve in said inspiration section for controlling flow of said respiratory gas; and
   a safety valve disposed between said control valve and said airways for, when open, admitting air to said airways, said safety valve having a valve opening, a valve plate carrying a sealing element, means supporting said valve plate for pivoting between an open position with said sealing element spaced from said valve opening, and a closed position with said sealing element blocking said valve opening, electromagnetic means connected to said plate for, when energized, applying a force load, corresponding to a predetermined overpressure in said inspiration section, to said plate for generating a first torque urging said plate toward said closed position and for applying, when de-energized, a force to said plate for generating a second torque urging said plate toward said open position, said second torque exceeding said first torque so that said safety valve is closed when said electromagnetic means is energized and is open when said electromagnetic means is de-energized, said means for applying further including means connected to said plate for adjusting the magnitude of said force load.

8. A respiratory ventilator as claimed in claim 7 further comprising:
   means for sensing pressure in said inspiration section; and
   means for de-energizing said electromagnetic means when a selected overpressure in said inspiration section, sensed by said means for sensing, is lower than said predetermined overpressure.

9. A respiratory ventilator as claimed in claim 8 further comprising:
   programmable control means for de-energizing said electromagnetic means at a programmed overpressure which is less than said predetermined overpressure.

10. A respiratory ventilator as claimed in claim 7 further comprising:
   means for sensing pressure in said inspiration section; and
   means for de-energizing said electromagnetic means when an overpressure in said inspiration section, sensed by said means for sensing, exceeds a selected overpressure by a predetermined safety interval and is below said predetermined overpressure.

* * * * *